United States Patent [19]
Dumont et al.

[11] Patent Number: 5,349,863
[45] Date of Patent: Sep. 27, 1994

[54] SHOCK SENSOR AND DEVICES TO WHICH THE LATTER IS APPLIED

[75] Inventors: Jean-Pierre Dumont, Mantes La Jolie; Riviere Daniel, Conflans Ste Honorine, both of France

[73] Assignee: Societe Nationale Industrielle et Aerospatiale, France

[21] Appl. No.: 781,142
[22] PCT Filed: Jun. 27, 1990
[86] PCT No.: PCT/FR90/00476
    § 371 Date: Feb. 27, 1992
    § 102(e) Date: Feb. 27, 1992
[87] PCT Pub. No.: WO91/00521
    PCT Pub. Date: Jan. 10, 1991

[30] Foreign Application Priority Data
Jun. 28, 1989 [FR] France ............... 89 08626

[51] Int. Cl.⁵ ............................................. G01D 21/00
[52] U.S. Cl. ........................................ 73/651; 73/510; 73/517 A
[58] Field of Search ............... 73/651, 517 A, 35 P, 73/650, 654, 510, 105

[56] References Cited
U.S. PATENT DOCUMENTS

| | | | |
|---|---|---|---|
| 3,292,977 | 12/1966 | Williams | 73/510 |
| 3,754,225 | 8/1973 | Gleason | 73/654 |
| 4,041,775 | 8/1977 | McNamee | 73/651 |
| 4,562,740 | 1/1986 | Webber et al. | 73/35 P |

*Primary Examiner*—Hezron E. Williams
*Assistant Examiner*—Rose M. Finley
*Attorney, Agent, or Firm*—Pearne, Gordon, McCoy & Granger

[57] ABSTRACT

Shock or impact sensor which can be fixed to a structure (14) comprising, along a longitudinal axis (AL) perpendicular to the structure (14), a rod (12) which can be joined to the structure (14) by a first end (16), a weight or counterweight (24) joined to a second end of the rod (12) and acceleration detection fixed to weight or counterweight (24) to detect acceleration along an axis perpendicular to the longitudinal axis of the sensor.

11 Claims, 1 Drawing Sheet

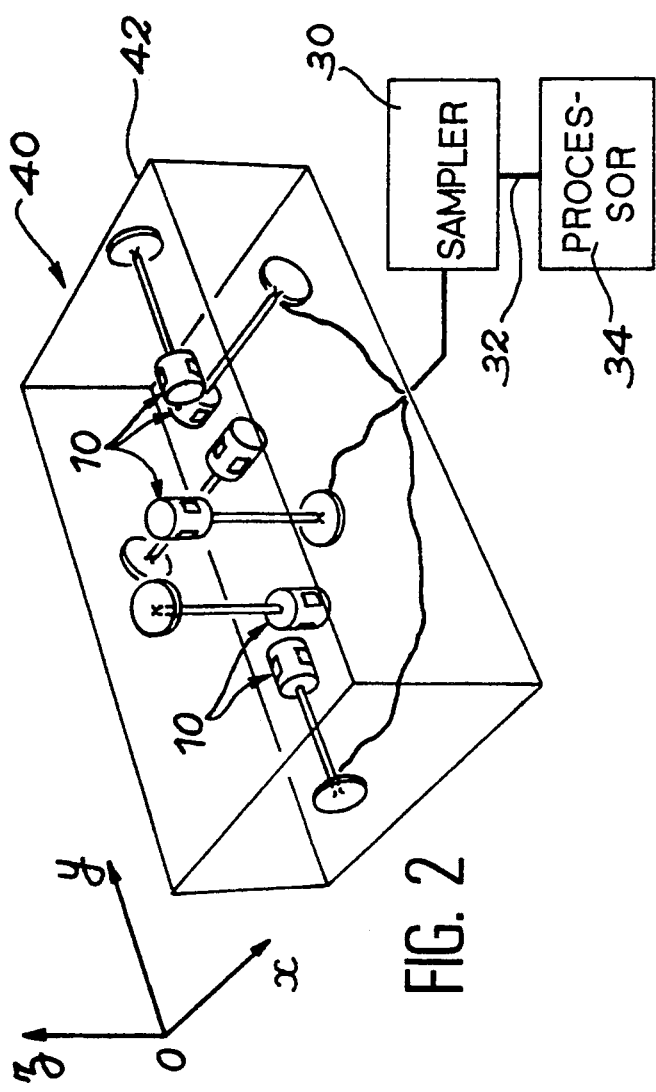

SHOCK SENSOR AND DEVICES TO WHICH THE LATTER IS APPLIED

DESCRIPTION

The present invention relates to a shock or impact sensor and devices to which it is applied. It more particularly applies to the characterization of a shock (determination of the shock spectrum, etc.) and to the measurement of accelerations and speeds.

A complex mechanical structure which is subject to a shock vibrates. The low frequency components of this vibration have an important function in the mechanical effects following the shock, such as the relative displacements of the different parts of the structure. However, their characterization is made difficult by the presence of interfering components having a higher frequency and which in practice do not influence the displacements, but falsify the measurement.

Known shock sensors have a wide passband (a few 10 kHz to a few 100 kHz) and this constitutes a major disadvantage, because the sensitivity of these sensors is proportional to their passband. They provide no information on the low frequency components corresponding to accelerations close to 100 g. The latter are drowned in the numerous high amplitude, high frequency components. The peak accelerations measured during the envisaged shocks are in the range 1000 to 100,000 g.

The object of the present invention is to provide a shock sensor permitting the easy extraction of the low frequency components from the high frequency components and thus permitting the evaluation of the different mechanical effects undergone by the parts of a structure.

Another object of the invention is to provide a device for characterizing a shock to which said sensor is applied, which is easy and inexpensive to use.

Another object of the present invention is to provide a gyrometer to which the present sensor can be applied and which is easy and inexpensive to use.

More specifically, the present invention relates to a shock sensor, which can be fixed to a structure, characterized in that it comprises, along a longitudinal axis perpendicular to the structure, a rod which can be joined to the structure by a first end, a weight joined to a second end of the rod and at least one means for detecting acceleration along an axis perpendicular to the longitudinal axis, said acceleration means being fixed to the weight.

This apparatus constitutes a mechanical oscillator tuned to a fundamental resonant frequency chosen as a function of the type of shock to be dealt with. This oscillator is excited when the structure to which it is fixed is exposed to an impact or shock. The means for detecting acceleration then supplies an electrical signal proportional to the acceleration of the weight in a given direction. Following appropriate processing, this signal makes it possible to determine the speed at the base of the sensor and to deduce the shock spectrum therefrom.

The present invention also relates to apparatuses in which said shock sensor is used and in particular a shock characterizing apparatus and a gyrometer.

The invention is described in greater detail hereinafter relative to non-limitative embodiments and the attached drawings, wherein show:

FIG. 1 diagrammatically an apparatus for the characterization of a shock according to the invention.

FIG. 2 diagrammatically a gyrometer according to the invention.

FIG. 1 shows diagrammatically an apparatus for characterizing a shock. The apparatus comprises a shock sensor 10 according to the invention and which is fixed to a structure or frame 14.

Such a shock sensor 10 has a fundamental resonant frequency below 1 kHz. It has a means for removing the harmonic resonant frequencies from the fundamental resonant frequency of the sensor. When the fundamental resonant frequency is fixed, this amounts to raising the value of the harmonic resonant frequencies. An example of such a means is given hereinafter. During the processing of the electrical signals supplied by the sensor, it makes it possible to easily separate the component at the fundamental resonant frequency from the components at the harmonic resonant frequencies.

The shock sensor 10 comprises a cylindrical rod 12 terminated by a first end 16, which can be threaded. The rod 12 is mounted to the integral with the structure 14. For this purpose the end 16 is introduced into an orifice provided for this purpose in the structure 14. A nut 20 is screwed onto the threaded portion issuing from the orifice. The structure 14 is held between the nut 20 and a base 18. At rest, the rod 12 is positioned along a longitudinal axis AL perpendicular to the structure 14.

A groove 22 is provided perpendicular to the axis AL on the rod 12 in the immediate vicinity of the base 18, i.e. at the foot of the sensor 10. As the fundamental frequency is fixed, said groove 20 makes it possible to raise the value of the harmonic resonant frequencies. Such a groove can multiply by ten the value of said frequencies.

A weight or counterweight 24 is joined to the other end of the rod 12 and can e.g. be fixed by bonding or gluing, using a glue of the araldite or cyanolite type.

In this embodiment, the weight 24 is cylindrical. It is provided with two acceleration detection means fixed by adhesion in recesses 28 made for this purpose in the weight 24. These acceleration detecting means are preferably piezoelectric acceleration detectors 26a and 26b of type 226C manufactured by Endevco that provide electrical signals proportional to acceleration. They are arranged along two axes AP1 and AP2, which are perpendicular to one another and to the axis AL.

Preferably, the weight 24 and the acceleration detectors 26a, 26b form an assembly, whose centre of gravity at rest is located on the axis AL. The weight of the rod 12 is negligible compared with that of the weight 24. The weight of the acceleration sensors 26a, 26b is added to that of the weight 24.

The bending strength of the rod 12 and the weight of the weight 24 are chosen in such a way that the resonant frequency of the sensor 10 is at the most 1 kHz. Moroever, the rod 12 is made from a material such that it withstands shocks.

The following data illustrate in a non-limitative manner an embodiment of a sensor 10 having a fundamental resonant frequency of 245 Hz:

useful length of the rod (from the base of the weight): 60 mm,
material from which the rod is made: steel 15CDV6,
rod weight: 1.4 gr,
rod diameter: 4.5 mm,
groove diameter: 4 mm, material from which the weight is made: steel 15CDV6, total weight of (counter)weight: 15 gr, weight diameter: 10 mm, weight height: 20 mm, weight of a acceleration detector: 2.8 gr.

In all cases, the total weight of the shock sensor 10 is well below that of its supporting structure 14.

When the structure 14 is exposed to a shock, the sensor 10 oscillates about the axis AL. The acceleration detectors 26a, 26b then supply electrical signals making it possible to evaluate the speed at the base 18 of the rod 12 in the two directions AP1 and AP2. The electrical signals supplied by the acceleration detectors 26a and 26b are proportional to the acceleration of the weight 24 along the axes AP1 and AP2. These electrical signals have a component at the fundamental resonant frequency and components at the harmonic frequencies, the latter being filtered by filtering means.

The filtering means can be constituted by a low-pass filter eliminating the frequencies equal to or above the predetermined frequency Fo. This frequency Fo can be twice the fundamental resonant frequency Fr of the shock sensor 10. The filtered signal is then sampled by a sampler.

However, in preferred manner, these filtering means are constituted by a sampler 30 carrying out a sampling at a frequency of 4 Fr. The sampler 30 then serves as a low-pass filter having a critical frequency of 2 Fr. The filtering obtained gives rise to a weak interfering signal at the frequencies above 2 Fr, considered as forming part of the measurement noise in the processing of the signal.

As a result of this filtering, the passband and therefore the measuring range of the shock sensor are reduced. As a result of the rise in the resonant harmonic frequencies this reduction does not lead to any deformation in the shape of the signal.

The sampled signal is supplied to an input of a transmission means 32 in which it can be multiplexed with other signals. This transmission means 32 e.g. incorporates an emission means 32a of a high frequency wave coupled to a reception means 32b.

In the case of a multiplexed emission, demultiplexing is ensured by the reception means 32b, which supplies on an output a digital signal corresponding to the sampled signal. This output is connected to an input of computer-type processing means 34 and can e.g. be in the form of a microcomputer.

During its manufacture, the shock sensor 10 is calibrated, i.e. an accurate determination is carried out of all the inherent frequencies (resonant frequencies) of the sensor and the damping coefficients thereof, said parameters being useful during processing.

The input data are supplied by the digital signal corresponding to the sequence of samples representing the acceleration of the counterweight in time.

By deconvolution, with the aid of the inherent frequencies and damping coefficients measured during calibration, a determination takes place of the speed of the base of the sensor 10 during the said time. This processing stage takes account of the fact that the shock sensor 10 has a negligible weight compared with that of its supporting structure 14.

The speed is determined along two directions AP1 and AP2 which are perpendicular to one another. It is possible to deduce therefrom the speed of the base of the sensor 10 in any random other direction.

On the basis of the speed at the base, a determination takes place of the shock spectrum in acceleration, assuming that said acceleration is a portionwise linear function between two sampling points. This spectrum constitutes the sought characterization for a shock. Once determined, the shock spectrum can be printed on a support and kept in a memory.

FIG. 2 diagrammatically shows a gyrometer according to the invention. This gyrometer has three pairs of sensors 10 according to the invention and of the type described hereinbefore (cf. FIG. 1). The sensors 10 are fixed to an e.g. parallelepipedic, box-shaped, rigid support 42. Each pair of sensors is constituted by two sensors placed head to tail and fixed to two opposite walls of the box 42. Each of the pairs is fixed along one of the three directions in space ox, oy and oz. Each sensor 10 has two acceleration detectors (one along each transverse axis), the determination of the angular velocities or speeds in each direction in space being doubled, which makes it possible to average out the measurements and improve the signal-to-noise ratio.

In this embodiment, under the effect of a shock, each sensor 10 supplies two electrical signals proportional to the accelerations of the weight in directions perpendicular to the longitudinal axis of the sensor. These signals are sampled by an array of samplers 30 serving as a filtering means. Sampling takes place at a frequency of 4 Fr (Fr being the fundamental resonant frequency of the sensors 10, which is here identical for each sensor for simplification reasons). The samplers behave like low-pass filters, whose critical frequency is 2 Fr.

Thus, at the output of the array of samplers twelve sampled signals are obtained representing the accelerations of the weights.

Transmission means 32 are connected to said output. These means 32 can be identical to those described hereinbefore (cf. FIG. 1) and may also consist of a single connecting line. Processing means 34, such as e.g., a microcomputer, are connected to an output of the transmission means 32.

As for the previously described shock characterization apparatus, for each sensor 10 is deduced the speed at the base of the sensors as a function of the time in two directions perpendicular to the longitudinal direction of the sensors as a result of a deconvolution with the aid of the data concerning the inherent frequencies and the damping coefficients of each sensor and which were determined during a prior calibration.

In the case of a shock, through knowing the speed at the base of each of the sensors and the distances separating the bases of the sensors forming a pair, it is possible to deduce the angular speeds of the support 42 relative to a fixed reference mark.

Due to the fact that it makes it possible to choose its fundamental resonant frequency and it is provided with means making it possible to raise the harmonic frequencies, the shock sensor according to the invention permits a filtering of said harmonic frequencies, which can easily take place by sampling. The sampled signals are processed so as to deduce, by deconvolution, the speed at the base of the sensor during a shock and on the basis thereof the shock spectrum is determined.

We claim:

1. A shock sensor for attachment to a structure and having a fundamental resonant frequency, said sensor comprising:

a rod having a first end, a second end and a longitudinal axis, said first end being attachable to said structure;

a weight attached to said second end;

acceleration detection means attached to said weight for detecting vibrations along an axis perpendicular to said longitudinal axis; and means to remove a plurality of harmonics of said fundamental resonant frequency from said vibrations.

2. A sensor according to claim 1, wherein said means to remove a plurality of harmonics includes a groove in said rod near said first end.

3. A sensor according to claim 1, wherein said means to remove a plurality of harmonics includes a low-pass filter.

4. A sensor according to claim 3, wherein said low pass filter comprises a sampler operating at a frequency of four times the fundamental resonant frequency.

5. A sensor according to claim 1, wherein said means to remove a plurality of harmonics includes a groove in said rod near said first end and a sampler operating at a frequency of four times the fundamental resonant frequency.

6. A sensor according to claim 1, wherein said fundamental resonant frequency is no more than 1 Khz.

7. A sensor according to claim 1, wherein said acceleration detection means includes two piezoelectric acceleration detectors located on the weight, each piezoelectric acceleration detector having a sensing direction, each of said directions being perpendicular to each other and said longitudinal axis.

8. A sensor according to claim 1, wherein said weight and vibration detection means in combination have a center of gravity located on said longitudinal axis.

9. A sensor according to claim 1, wherein the rod and the weight are cylindrical.

10. A sensor according to claim 1, wherein the weight has a recess and the vibration detection means is attached to the weight in said recess.

11. A gyrometer for measuring a rotation, comprising:

a support;

a first and a second sensor, each sensor having a fundamental resonant frequency and including:

a rod having a first end, a second end and a longitudinal axis, said first end being attached to said support and said rod having a groove near said first end;

a weight attached to said second end; and acceleration detection means attached to said weight for detecting vibrations along an axis perpendicular to said longitudinal axis; said first and second sensor first ends being spaced apart; and means for measuring a velocity for each sensor first end and combining said velocities to provide a measure of said rotation.

* * * * *

UNITED STATES PATENT AND TRADEMARK OFFICE
CERTIFICATE OF CORRECTION

PATENT NO. : 5,349,863

DATED : September 27, 1994

INVENTOR(S) : Jean-Pierre Dumont, et al.

It is certified that error appears in the above-indentified patent and that said Letters Patent is hereby corrected as shown below:

On the title page, under item [75], line 2, "Riviere Daniel" should be --Daniel Riviere--.

Signed and Sealed this

Eleventh Day of April, 1995

*Attest:*

BRUCE LEHMAN

*Attesting Officer*    *Commissioner of Patents and Trademarks*